(12) United States Patent
Ruiz Ballesteros et al.

(10) Patent No.: US 7,400,822 B2
(45) Date of Patent: Jul. 15, 2008

(54) ACTIVE SUBSTANCE EVAPORATOR

(75) Inventors: Julio Cesar Ruiz Ballesteros, Barcelona (ES); Ruben Garcia Fabrega, Barcelona (ES); Andrea Caserta, Barcelona (ES)

(73) Assignee: Zobele Espana, S.A. (ES)

( * ) Notice: Subject to any disclaimer, the term of this patent is extended or adjusted under 35 U.S.C. 154(b) by 0 days.

(21) Appl. No.: 10/511,191

(22) PCT Filed: Jun. 12, 2002

(86) PCT No.: PCT/ES02/00287

§ 371 (c)(1),
(2), (4) Date: Apr. 27, 2005

(87) PCT Pub. No.: WO03/086485

PCT Pub. Date: Oct. 23, 2003

(65) Prior Publication Data

US 2005/0185938 A1    Aug. 25, 2005

(30) Foreign Application Priority Data

Apr. 12, 2002    (ES)    ................................ 200200863

(51) Int. Cl.
*F24F 6/00*    (2006.01)
(52) U.S. Cl. ...................................... 392/390; 392/392
(58) Field of Classification Search ................ 392/386, 392/390, 391, 392, 393, 394, 395; 239/34, 239/35, 44, 45, 50; 122/366
See application file for complete search history.

(56) References Cited

U.S. PATENT DOCUMENTS

| | | | | |
|---|---|---|---|---|
| 4,391,781 A | | 7/1983 | Van Lit | |
| 4,725,712 A | * | 2/1988 | Schroeder | 392/392 |
| 5,078,288 A | * | 1/1992 | Fuchs | 215/209 |
| 5,558,700 A | * | 9/1996 | Shibahashi et al. | 106/31.15 |
| 5,695,692 A | * | 12/1997 | Kennedy | 261/30 |
| 5,794,803 A | * | 8/1998 | Sprick | 215/217 |
| 6,078,728 A | * | 6/2000 | O'Rourke et al. | 392/390 |
| 6,154,607 A | * | 11/2000 | Flashinski et al. | 392/390 |

FOREIGN PATENT DOCUMENTS

| | | |
|---|---|---|
| DE | 4301912 A1 | 9/1994 |
| ES | 245083 U | 12/1979 |
| ES | 256307 U | 5/1982 |

* cited by examiner

OTHER PUBLICATIONS

Patent Abstracts of Japan, vol. 2002, No. 5, Mar. 5, 2002 and JP 2002027890A (Fukada) Jan. 29, 2002.

*Primary Examiner*—Sang Y Paik
(74) *Attorney, Agent, or Firm*—Schiff Hardin LLP

(57) ABSTRACT

An evaporator device for active substances is designed for using active substances established in a paper tablet or the like, or in a tray with a semipermeable membrane, in gel form, comprising a base body with a U-shaped profile inside coupled by insertion to a support provided with two housings and, the former adapted in size and shape to receive within it a tray and the second to receive a tablet, so that both the tray and tablet can be placed in the same support opposite the heating surface of the device. This allows using the device equally with either format of the active substance. The device also includes a safety mechanism comprising teeth that lock in the closed position, preventing or making it difficult for children to displace or extract the support from the casing, that requires pressing inwards on two lateral opposing areas of the casing to open.

11 Claims, 5 Drawing Sheets

ACTIVE SUBSTANCE EVAPORATOR

BACKGROUND

The present invention relates to a device for evaporating active substances, with the special characteristic of allowing a dual use, specifically use with two different types of containers of active substances, in tablets or in trays.

Evaporator devices for active substances are already known, specifically electrical evaporators for insecticides, which are based on the use of a PTC electrical resistance that acts on a heating surface next to which is placed the insecticide product, such as those described, for example, in Spanish Patent Nos. 9600482 and 9601197.

In addition, the insecticide product is generally commercialized in at least two different types of containers: tablets of paper or the like, duly soaked for a one-day protection; or trays with insecticide gel, closed by a semi-permeable membrane for a longer-lasting protection.

According to each type of container for the insecticide product, there are currently two different versions of electrical evaporator, within each specific solution, adapted to one or the other container.

As another feature, conventional evaporators have an intermittent operation and incorporate an indicator lamp connected in parallel to the PTC, which has the obvious purpose of indicating to the user whether or not the evaporator is operating.

This solution presents a two-fold drawback: on one hand, it actually does not indicate whether the PTC is warm, but instead indicates whether it is connected, thus, the evaporator could be very hot at the end of an operational cycle of the PTC resistor, yet the lamp will be off. Furthermore, the lamp requires electrical cables for its connection to the power supply, hindering the assembly of the various parts making up the device and therefore increasing the cost of production.

Moreover, when the evaporator is disconnected from the power supply by the user to replace the cartridge the device may remain warm due to its heat capacity, yet obviously any indicator lamp will cease to function.

SUMMARY

Thus, the object of the invention is to obtain a standardization of the device so that the same evaporator device can be operated with either of the two aforementioned conventional presentations of the active substance, this is, as a tablet or as a tray.

A second object of the invention is to simplify the mechanism used by the device to indicate its temperature.

Yet another object of the invention is to provide the device with a safety mechanism to make it difficult for children to extract the tablets or trays containing the active substance.

The evaporator for active substances disclosed by the invention solves the aforementioned drawbacks in a fully satisfactory manner, in each and every aspect mentioned above.

For this, more specifically and in accordance with one of the embodiments of the invention, the body of the device housing the heater is structured such that it can receive, with a detachable construction, a support for the active substance, where the support has two housings used selectively, one being adapted in size and shape to the conventional tablets and another similarly adapted to the gel trays, using the most suitable one in each case and leaving both the tablet and the gel tray properly facing the heating surface of the body behind which is placed the PTC resistor.

More specifically, the base body has a U-shaped profile, considerably flattened, between the side wings of which is coupled by plugging or sliding the aforementioned support for the active substance.

According to another characteristic of an embodiment of the invention and replacing the conventional indicator lamp, at the wing of the base body constituting the front visible face of the device, in any suitable location therein, thermochrome paint with any pattern is established such that this pattern will change in color at the temperature under which the evaporator can be handled safely. The thermochrome paint can be applied directly on the casing of the device, on a sticker label, or it can even comprise a complementary part made of thermochrome plastic; the use of any of these solutions or any other deemed suitable does not affect the essence of the invention.

According to another characteristic of an embodiment of the invention, the device includes a safety mechanism meant to make it difficult for children to remove the tablets or trays holding the active substance. This mechanism is based on locking teeth defined in the inner wall of the casing and on the side walls of the sliding support. This design makes it necessary to press simultaneously on both sides of the casing and specifically on opposite points of it in order to release and allow the outwards displacement of the aforementioned container for the tablet of active substance or the corresponding tray. A stop provided on each side face of the support walls can lock in a rear protrusion of each side of the inner wall of the device casing; the first case therefore corresponds to the closed position of the device and the second to the extraction position of the support of the tablet or tray with the active substance, the extraction being naturally limited by the locking of the aforementioned corresponding stop and protrusion.

DESCRIPTION OF THE DRAWINGS

As a complement of the description being made and in order to aid a better understanding of the characteristics of the invention, in accordance with an example of a preferred embodiment, a set of drawings is accompanied as an integral part of the description where for purposes of illustration only and in a non-limiting sense the following is shown.

DETAILED DESCRIPTION OF THE PREFERRED EMBODIMENTS

In view of these figures, it is seen that the evaporator device according to an embodiment of the invention comprises a casing 1, which, as is conventional, has an integrated classical electrical plug 2 for direct connection of the device to an electric socket, attached, for example, to a wall, through which is powered a PTC type heating resistance, not shown in the figures, that transforms electrical energy into heat that is applied to a heating surface 3 (FIG. 4), next to which will be placed the active substance used in each case.

Figure 4:
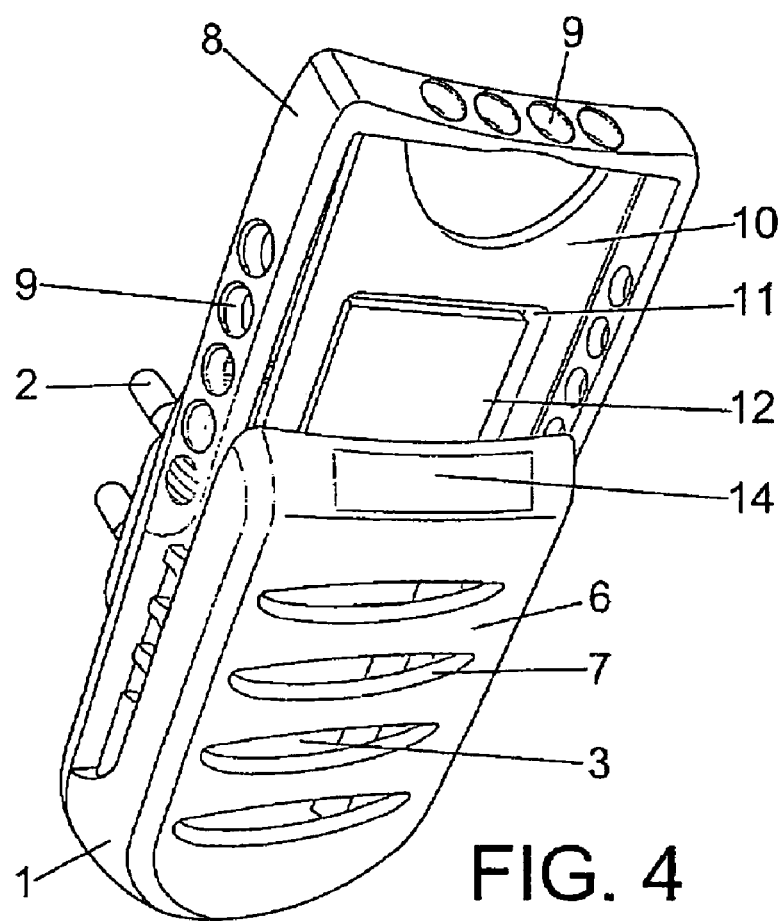
FIG. 4 is a front a perspective view similar to that shown in FIG. 1 in which the support for the active substance is shown with its greater part uncoupled from the base body and supporting a tablet inside it.
Figure 5:
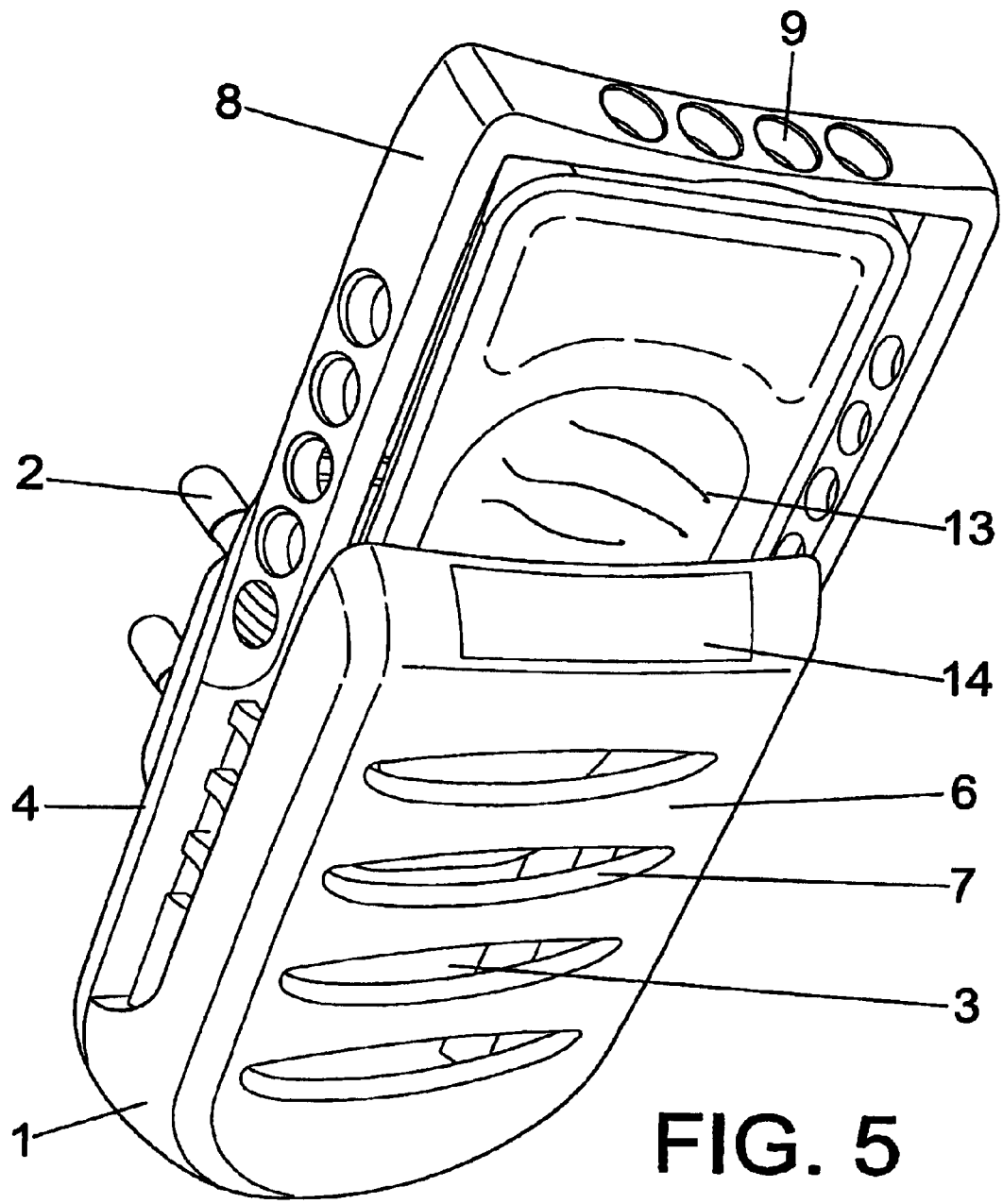
FIG. 5 is a front perspective view similar to that shown in FIG. 4 where the aforementioned support incorporates an insecticide gel tray.

As such, the relatively flat base body 1, has a U-shaped profile such that its rear wing 4, provided with ventilation grilles 5, is where the power supply circuit of the PTC and the heating surface 3 are established. Its front wing 6 is also provided with a grille 7 for aeration of the hollow interior of the base, in which is housed a support 8, preferably by plugging or insertion, which, when assembled, establishes a surface continuity with the base 1, as seen particularly in FIG. 1. The support 8, in turn, is provided with ventilation orifices 9, but is particularly provided with a recess or housing 10 inside which is established a smaller second housing 11, which is adapted in size and shape to the classic insecticide tablets 12. The larger housing 10 is in turn adapted in size and shape to the trays 13 closed with a semipermeable membrane that contain insecticide products in a gel form. FIGS. 4 and 5 show the visually indistinct use of the same evaporator device with the two different types of format for the product or active substance.

Figure 1:
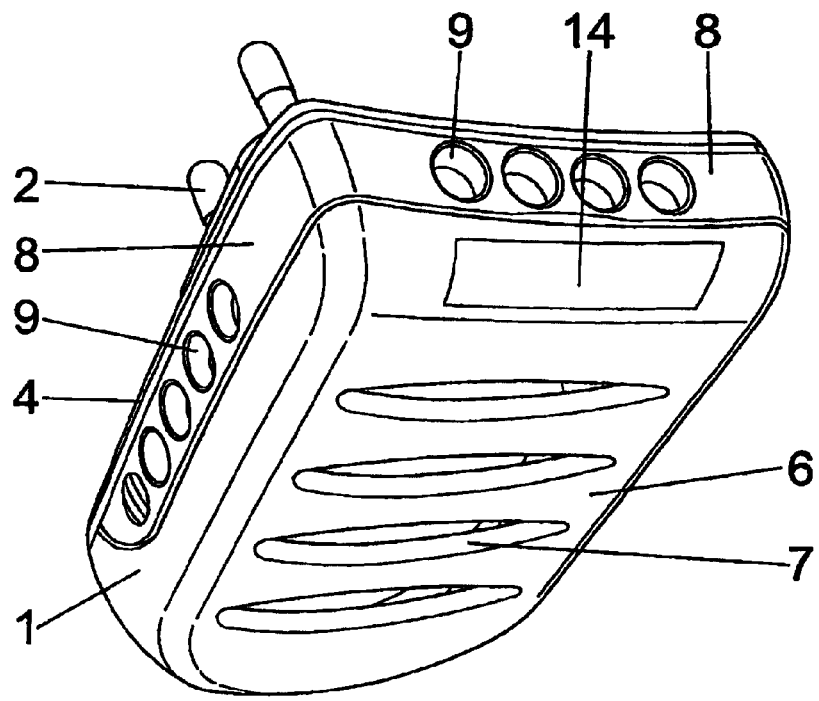
FIG. 1 is a front perspective view of an evaporator device for active substances constructed according to an embodiment of the present invention.
Figure 2:
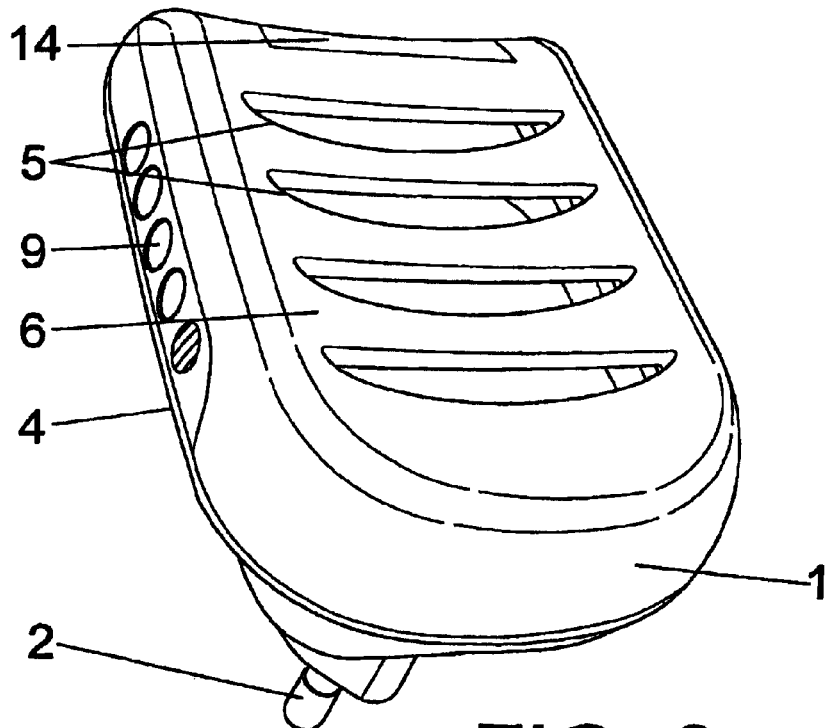
FIG. 2 is a rear perspective view of the device shown in FIG. 1.
Figure 3:
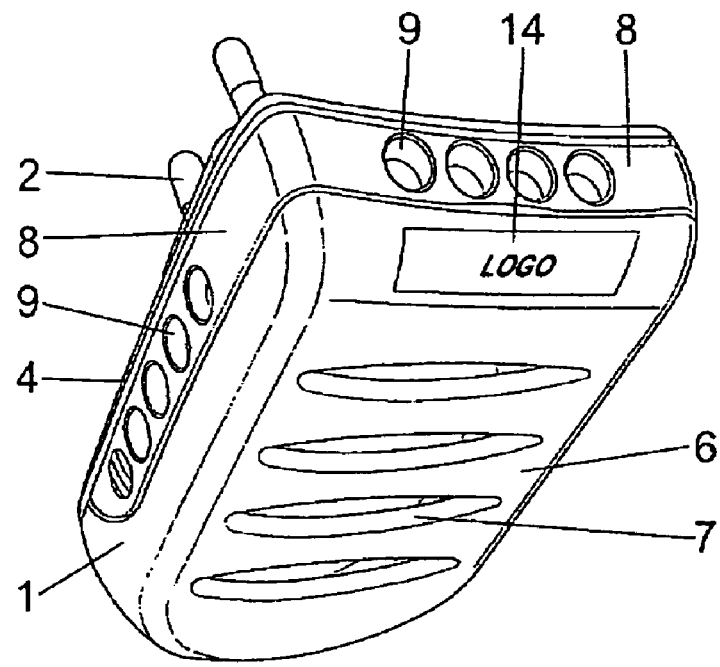
FIG. 3 is a front perspective view with a similar representation to FIG. 1 in which the thermal indication pattern has changed color.

As a complement of the described structure, in the lateral wing 6 of the base body 1 corresponding to the front face of the evaporator device in a ready-to-use situation, a pattern 14 is established that could be, e.g., the brand name of the product made with thermochrome paint so that this pattern 14 adopts a certain color when the evaporator device is cold, such as in the situation of FIG. 1, and changes color when it exceeds a specified heat level, as in the case of FIG. 3, thereby allowing the user to know the true temperature level of the evaporator regardless of whether the PTC is electrically connected, as well as eliminating the electrical power supply cabling of the traditional electrical visual indicators.

Figure 6:
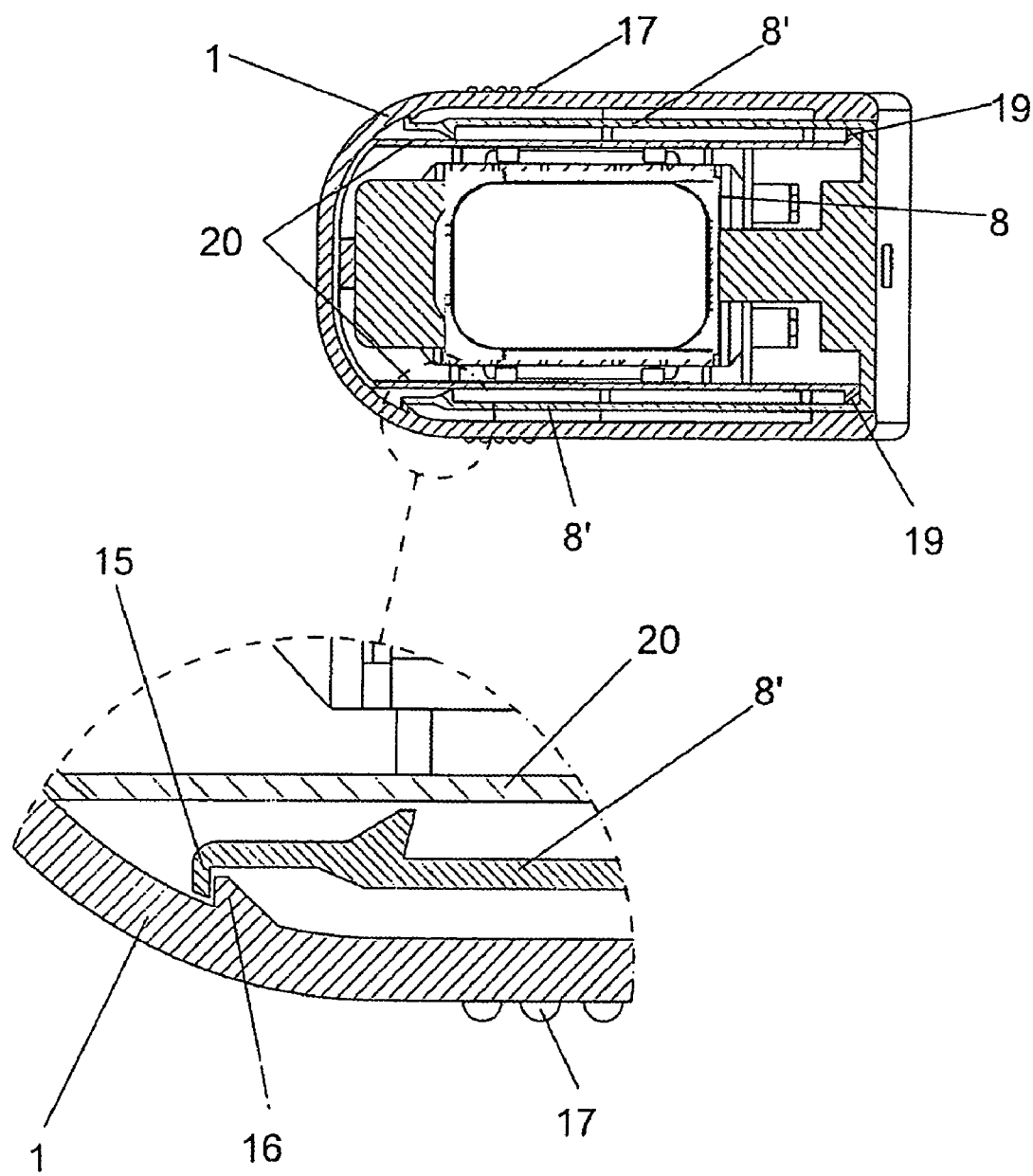
FIG. 6 is a top sectional view of the device in a closed position, showing an enlarged inset of the locking established by the complementary teeth of the sliding support and the casing.
Figure 7:
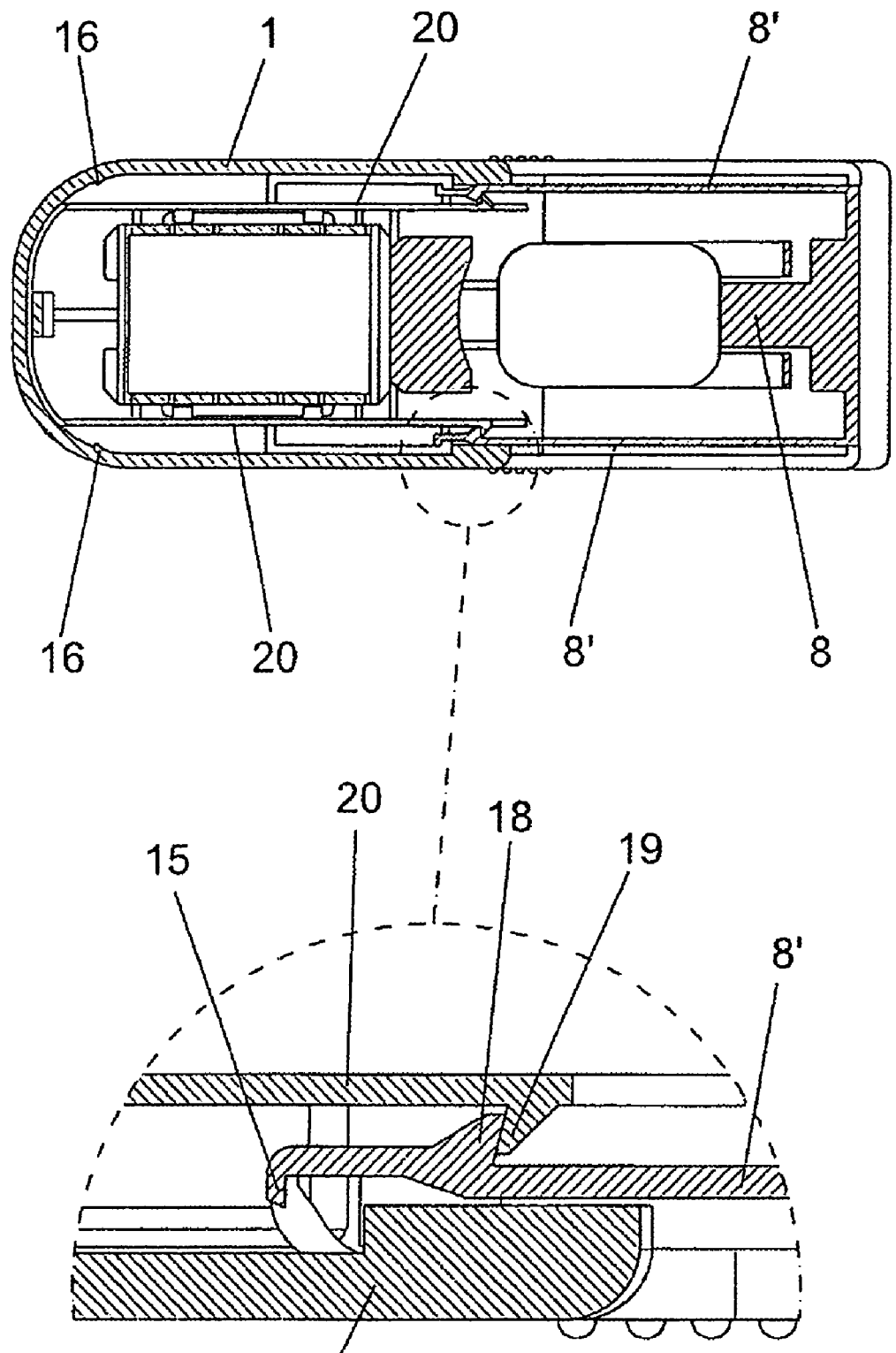
FIG. 7 is a top sectional enlarged inset of the device represented in FIG. 6 in an end extraction position for the support of the tablet or tray with the active substance, the extraction being limited by the corresponding locking between the stop teeth established in both bodies (the casing and the support).

The device includes a safety mechanism to make it difficult for children to extract the support 8 where the tablet or tray of the corresponding active substance is housed. Specifically, the safety mechanism comprises a tooth 15 provided on the front end of each of the lateral walls 8' of the support 8 that slide inside the casing 1, whose teeth 15 are designed to lock in the closed position shown in FIG. 6 in other complementary teeth 16 provided for this purpose in the inner part of the casing 1. In the locked position of FIG. 6, even if the support 8 is pulled outwards it will not move, unless one applies an inwards pressure on the lateral areas 17 of the casing 1, which will cause a deformation of the casing and the release of the teeth 15, 16, allowing one to pull the support 8 backwards and thus slide it to reveal the tablet or tray containing the active substance.

The backwards displacement of the support 8 is limited by the stop defined by a protrusion 18 of the lateral walls 8' of the support 8, pressing against the protrusion or protrusions 19 provided for such purpose on the inner walls 20 as sliding guides for the support 8, and specifically for its side walls 8'.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The particular implementations shown and described herein are illustrative examples of the invention and are not intended to otherwise limit the scope of the invention in any way. For the sake of brevity, conventional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

The invention claimed is:

1. An evaporator device for active substances, comprising:
 a base body in which is integrated a plug for direct connection to an electrical power supply;
 a circuit comprising a PTC heating resistance connected to the integrated plug that is configured to act on a heating surface near which is placed an active substance;
 the base body further comprises a removable and slidable support for the active substance, the support comprising first and second recesses, said first recess being adapted in size and shape to a first type of container of the active substance and the second recess being adapted in size and shape to a second type of container of the active substance, said first and second types of containers being of different sizes, the first type of container of the active substance being a tablet and the second type of container of the active substance being a tray with a semi permeable membrane, so that the evaporator device can equally receive either type of container of the active substance.

2. The evaporator device for active substances, as claimed in claim 1, wherein the base body is U-shaped, the base body comprising a rear portion and front portion, the front portion comprising aeration grilles, and the support fitting between the rear portion and front portion of the base body which, in an assembled position, establishes a surface continuity with the base body and the housings for the tablet and tray are in a position adjacent to the heating surface.

3. The evaporator device for active substances, as claimed in claim 1, further comprising:
 a pattern made with thermochrome paint applied directly on the base body or on a complementary support attached to said base body, wherein the pattern changes colour at a temperature under which physical contact with the device is considered to be no longer dangerous.

4. The evaporator device for active substances, as claimed in claim 1, further comprising:
 a safety mechanism that makes it difficult to slide and thereby open the support containing the tablet or tray of the active substance with respect to the base body, the safety mechanism comprising teeth established in a front end of lateral walls of the support which, in a closed position, lock against complementary locking teeth provided for this purpose in the inner part of the base body, preventing the displacement towards an extraction position of the support.

5. The evaporator device for active substances, as claimed in claim 4, wherein a side surface of the base body and near an area where the locking teeth are established has corresponding areas which, when pressed manually inwards and by the ensuing deformation, allow releasing the teeth from the complementary locking teeth and thereby also releasing the support, allowing it to move to the extraction position.

6. The evaporator device for active substances, as claimed in claim 4, wherein the lateral walls of the suppeort comprise protrusions which, in the position of extraction of the support, limit the extraction by contacting other protrusions provided for such purpose in inner walls as sliding guides for the support.

7. The evaporator device for active substances, as claimed in claim 1, wherein the two recesses are of different sizes.

8. The evaporator device for active substances, as claimed in claim 7, wherein one of the two recesses is located inside of the other of the two recesses.

9. The evaporator device for active substances, as claimed in claim 7, wherein the containers of the active substances are of different sizes that correspond in shape respectively to the two recesses that are of different sizes.

10. The evaporator device for active substances, as claimed in claim 7, wherein the two recesses are capable of holding two different containers simultaneously.

11. The evaporator device for active substances, as claimed in claim 1, wherein an inner surface of the two recesses is generally a same shape as outer surfaces of the containers that the recesses hold.

* * * * *